United States Patent [19]

Ohorodnik et al.

[11] 4,104,299

[45] Aug. 1, 1978

[54] PRODUCTION OF PURE METHYLDICHLOROPHOSPHANE

[75] Inventors: Alexander Ohorodnik; Klaus Gehrmann, both of Erftstadt; Stefan Schäfer, Brühl; Albert Mainski, Cologne, all of Fed. Rep. of Germany

[73] Assignee: Hoechst Aktiengesellschaft, Frankfurt am Main, Fed. Rep. of Germany

[21] Appl. No.: 818,124

[22] Filed: Jul. 22, 1977

[30] Foreign Application Priority Data

Jul. 27, 1976 [DE] Fed. Rep. of Germany ....... 2633661
May 28, 1977 [DE] Fed. Rep. of Germany ....... 2724407

[51] Int. Cl.$^2$ .............................. C07F 9/52; C07F 9/02
[52] U.S. Cl. ................................................. 260/543 P
[58] Field of Search ..................................... 260/543 P

[56] References Cited

U.S. PATENT DOCUMENTS 3,210,418   10/1965   Pianfetti ........................... 260/543 P

FOREIGN PATENT DOCUMENTS 2,046,314   5/1976   Fed. Rep. of Germany.
2,629,299   12/1977   Fed. Rep. of Germany.
7,013,363   3/1972   Netherlands.

OTHER PUBLICATIONS

Pianfetti et al., J. Am. Chem. Soc., vol. 84, pp. 851–854 (1962).

*Primary Examiner*—Gerald A. Schwartz
*Attorney, Agent, or Firm*—Connolly and Hutz

[57] ABSTRACT

Pure methyldichlorophosphane is recovered from a mixture containing phosphorus trichloride and methyldichlorophosphane as its principal constituents by distillation in two stages. Phosphorus trichloride and other low-boiling material are distilled off overhead in the first stage and methyldichlorophosphane is distilled off from high-boiling material in the second stage, the latter being fed with base product coming from the first stage. More specifically, there is dissolved in the said mixture, prior to admitting it to the first distillation stage, 0.01 to 1 weight % of an organic barium compound or 0.1 to 10 weight % of a non-ionic surfactant, and the base product coming from the first distillation stage is admixed, prior to admitting it to the second distillation stage, with 1 to 10 weight % of phosphorus oxychloride.

7 Claims, 1 Drawing Figure

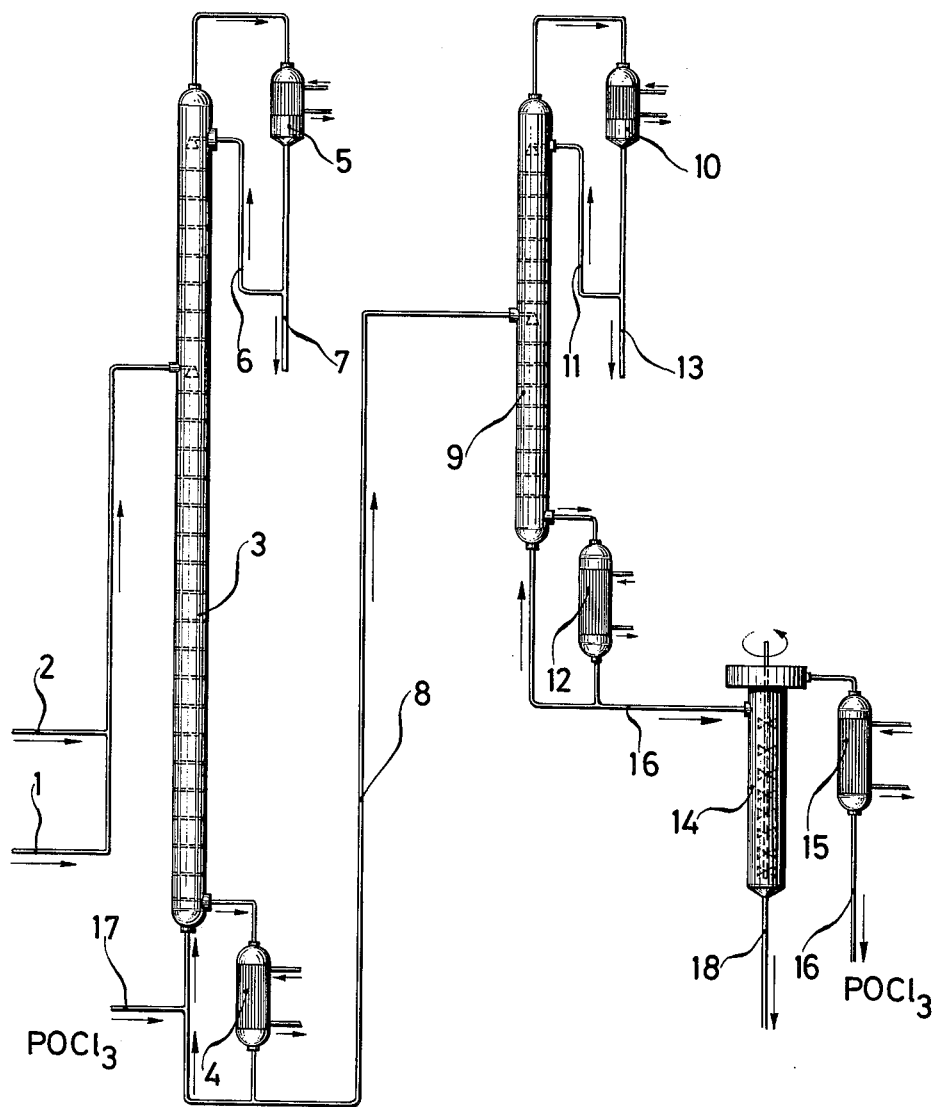

PRODUCTION OF PURE METHYLDICHLOROPHOSPHANE

This invention relates to a process for recovering methyldichlorophosphane from a mixture containing phosphorus trichloride and methyldichlorophosphane as its principal ingredients by distillation in two stages.

Methyldichlorophosphane ($H_3C\text{-}PCl_2$) is a compound which is of interest for use not only in preparative chemistry but also, and to an increasing extent, as a starting material for the production of flameretarding fibres and synthetic resins. Thus, for example, it is possible by reacting acrylic acid with methyldichlorophosphane to produce [$\beta$(chloroformyl)ethyl]-methylphosphinic acid chloride, which in turn can be subjected to boiling treatment with acetic anhydride to yield cyclic 2-methyl-2,5-dioxo-1-oxa-2-phospholane. Cyclic anhydrides of this type can be incorporated with advantage into polyester material, and they impart very good flameretardant or even self-extinguishing properties to filaments, fibres, films, sheets and moulded articles which are made therefrom. In order not to impair the various quality-defining characteristics, e.g. the coloration, of articles rendered flame-retardant therewith, it is necessary to use the phospholane in a particularly pure form. In this connection, it is an important requirement that methyldichlorophosphane in a particularly pure form should be used as the phosphorus-containing starting material for making the phospholane.

Processes for making methyldichlorophosphane from methane and phosphorus trichloride at temperatures higher than 500° C have already been described by J. A. Pianfetti and L. D. Quin in J.Am.Chem.Soc. 84 (1962), pages 851 to 854, and also in U.S. Pat. Specifications Nos. 3,210,418 and 3,519,685 as well as in German Published Pat. Specification ("Auslegeschrift") No. 2046314. A further process for making aliphatic dihalogenophosphanes, especially alkyldichlorophosphanes, from (e.g.) ethane and $PCl_3$, in the presence of $CCl_4$ as a reaction initiator, has been described in Dutch Published Patent Specification (the Dutch equivalent of an "Offenlegungsschrift") No. 7013363.

Owing to the low $PCl_3$-conversion rate, the resulting partly purified product contains $PCl_3$ together with only about 20 weight % of methyldichlorophosphane. The principal constituents, however, have boiling points which differ but slightly from each other ($H_3CPCl_2$ = 81.5° C, $CCl_4$ = 76.7° C, $PCl_3$ = 74.5° C, under 760 mm Hg), and these constituents are therefore difficult to separate by distillation. In consequence, it is necessary to effect this operation over long periods at temperatures close to the boiling point of $H_3CPCl_2$. This compound is accordingly substantially more liable to undergo spontaneous decomposition, which is, incidentally, favoured by the presence of impurities. In addition to this, it is known that when methyldichlorophosphane decomposes spontaneously it forms $PCl_3$ and other decomposition products which substantially comprise only solid materials which are insoluble in the reaction mixture, so that the circulation evaporators usually employed are very liable to become soiled therewith.

As can be inferred from the fact that both methyldichlorophosphane by itself and freshly distilled mixtures containing methyldichlorophosphane and phosphorus trichloride are liable to undergo decomposition even in the region of the above-mentioned boiling points, i.e. at temperatures above 70° C, in accordance with the following reaction scheme

with the resultant formation of compounds which predominantly comprise salt-like but otherwise largely unidentified solid materials, it is not possible merely by ordinary methods, e.g. distillation, to keep the various apparatuses free from soiling and to ensure that they remain operational.

The tendency of $CH_3\text{-}PCl_2$ to decompose spontaneously increases with increasing temperatures, and also with increasing proportions of contaminants in the crude product. Needless to say, the soiling of apparatus components with deposits of solid materials is highly undesirable in the continuous commercial production of methyldichlorophosphane.

In view of the difficulties described hereinabove, it is understandable that attempts have been made to find other procedures for the commercial production of methyldichlorophosphane. Thus, for example, a process for purifying methyldichlorophosphane has been described in U.S. Pat. Specification No. 3,519,685, wherein 1000 parts of a mixture of 760 parts of $PCl_3$ and 180 parts of $CH_3PCl_2$, the balance (60 parts) being by-products, are admixed with 522 to 1044 parts of (e.g.) phenol; the phenol chemically combines with $PCl_3$, so that $CH_3PCl_2$ can be distilled off. Clearly this process can be carried out under commercially attractive conditions only in exceptional cases, inasmuch as large quantities of the reaction product of $PCl_3$ with phenol are formed but have apparently to be discarded. The fact that such an expensive process has actually been suggested is a clear indication to the expert how difficult to achieve is the distillative separation which would appear at first sight to recommend itself.

In the ordinary distillative recovery of methyldichlorophosphane from a mixture containing not only low-boiling constituents, e.g. $PCl_3$, but also high-boiling constituents, it is good practice in a first stage to distil off overhead the low-boiling constituents and to leave in the base product the methyldichlorophosphane and all the high-boiling constituents; then, in a second stage, methyldichlorophosphane is distilled off overhead.

In order to enable methyldichlorophosphane with a purity of 99% to be separated from phosphorus trichloride in the first stage, it is necessary to employ a column with a separation efficiency of 80 to 130 theoretical trays, and to maintain a reflux ratio of 10:1 to 20:1. To separate methyldichlorophosphane with a purity of more than 99% from the high-boiling constituents in the second stage, it is necessary to use a column with a separation efficiency of 20 to 30 theoretical trays, and to maintain a reflux ratio of 2:1 to 5:1. On supplying a distillation apparatus having the features just described with a feed mixture free from solid materials and containing 17 weight % of methyldichlorophosphane (cf. Example 6 below), it is found that the material obtained in the circulation evaporator of the first distillation stage exhibits a strong undesirable coloration after as short a period as several hours. In the event that the solubility of the solid material formed is exceeded, the latter starts depositing predominantly on the (internal) surfaces of the evaporator. This has serious adverse effects on heat transmission in the evaporator, so that it has to be opened and cleaned mechanically even after several hours of operation. The problem which arises in connection therewith is well known to those skilled in the art. An analogous phenomenon has been found to occur upon the delivery of the base product from the first distillation stage to the second distillation stage.

It is an object of the present invention to make it possible to avoid the disadvantages described hereinabove.

According to the present invention, we provide a process for recovering methyldichlorophosphane from a mixture containing phosphorus trichloride and methyldichlorophosphane as its principal constituents by distillation in two stages, phosphorus trichloride and other low-boiling material being distilled off overhead in the first stage, methyldichlorophosphane being distilled off from high-boiling material in the second stage, and the latter being fed with base product coming from the first stage, which process comprises: dissolving in the said mixture, prior to admitting it to the first distillation stage, 0.01 to 1 weight % of an organic barium compound (ionic surfactant) or 0.1 to 10 weight % of a non-ionic surfactant, and admixing the base product coming from the first distillation stage, prior to admitting it to the second distillation stage, with 1 to 10 weight % of phosphorus oxychloride.

Preferred features of the present invention provide:

(a) for 0.5 to 5 weight % of the non-ionic surfactant to be dissolved in the said mixture;
(b) for the said base product to be admixed with 3 to 6 weight % of phosphorus oxychloride;
(c) for the base product containing high-boiling material to be removed from the second distillation stage, for phosphorus oxychloride to be distilled off therefrom, and for the latter to be recycled by being admixed with the base product coming from the first distillation stage;
(d) for a temperature of at most 115° C, preferably 105° C, to be maintained in the base of the first distillation stage;
(e) for a temperature lower than 120° C, preferably 102° to 110° C, to be maintained in the base of the second distillation stage;
(f) for an ethoxylated unbranched fatty alcohol having 6 to 30 carbon atoms to be used as the non-ionic surfactant;
(g) for a non-ionic polymer derived from ethylene oxide, or from ethylene oxide and propylene oxide, to be used as the non-ionic surfactant;
(h) for a soluble barium phenate-sulphonate mixture to be used as the barium compound; and
(i) for the mixture from which methyldichlorophosphane is recovered to be a mixture containing phosphorus trichloride, methyldichlorophosphane, carbon tetrachloride and chloroform.

The process of the present invention has been found to remain reliably operable over substantially unlimited periods of time. This is an unexpected result which has primarily to be attributed to the fact that the dissolved organic barium compound (ionic surfactant), or dissolved non-ionic surfactant, effectively prevents the deposition of solid material, which, however, has been found to concentrate in the base products of the two distillation stages. To improve its solubility and avoid the adverse effects caused by the deposition of solid material, the material left in the base of the first distillation stage is admixed with phosphorus oxychloride. Bearing in mind that $POCl_3$ has strongly corrosive properties, it is an unexpected result that the addition of $POCl_3$ does not substantially change the corrosiveness of the mixture of $PCl_3$ and $CH_3PCl_2$. This is a further advantage of the present process, which permits the largest components of the production equipment to be made up of relatively inexpensive steel.

The invention is illustrated by the following Examples, in which reference is made to the accompanying drawing, the single FIGURE of which is a diagrammatic side view of an apparatus, comprising inter alia two distillation columns, employed in accordance with the invention.

EXAMPLE 1

The procedure was carried out in an apparatus as shown diagrammatically in the accompanying drawing, wherein a distillation column 3 provided with 130 trays was used, in a first distillation stage, for separating $PCl_3$, $CHCl_3$ and $CCl_4$ from methyldichlorophosphane and high-boiling material. The column 3 was fed with 100 kg/h of a crude product composed of:

17 weight % of methyldichlorophosphane,
2.0 weight % of carbon tetrachloride,
1.1 weight % of chloroform,
0.2 weight % of $POCl_3$, and
0.2 weight % of unidentified constituents, the balance being $PCl_3$. This crude product was supplied through a conduit 1 to the 68th tray of the column 3. By means of a conduit 2, the crude product was admixed with 1.2 kg/h of an ethoxylated unbranched $C_{16-18}$ fatty alcohol (molar ratio = 7 $OC_2H_5$ groups per OH group). In addition, 1 kg/h of $POCl_3$ was introduced into a circulation evaporator 4 through a conduit 17. In the circulation evaporator 4, the crude product was brought to the boil at 102° to 104° C under the pressure prevailing therein. $PCl_3$, which still contained $CHCl_3$ and $CCl_4$, was obtained in a condenser 5. A certain proportion of it, viz. a proportion compatible with a reflux ratio of 15:1, was recycled through a conduit 6 to the head of the column 3, and the remainder was removed through a conduit 7, the portion removed through said conduit 7 being recycled to a reactor (not shown in the drawing). Once the crude product in the circulation evaporator 4 was found to be free from $PCl_3$, it was removed at a rate of 18.4 kg/h through a conduit 8 and delivered to the second quarter portion of a second column 9. Purified methyldichlorophosphane was obtained in a condenser 10. A proportion compatible with a reflux ratio of 2:1 was recycled through a conduit 11 to the head of the distilling column 9, while 16.5 kg/h of this purified methyldichlorophosphane was removed through a conduit 13. Under the pressure prevailing, a circulation evaporator 12 associated with the distilling column 9 was heated to 104° to 108° C, and base product was removed therefrom at a rate of 19 kg/h through an outlet 19. The base product was delivered to a thin film evaporator 14, in which $POCl_3$ was distilled off, this $POCl_3$ being condensed in a heat exchanger 15, and removed through a conduit 16. The $POCl_3$ so recovered, which still contained some methyldichlorophosphane, was recycled through the conduit 17 to the circulation evaporator 4 associated with the column 3. High-boiling material and non-volatile ethoxylated fatty alcohol were withdrawn through a conduit 18.

In the manner described, it was possible to produce purified methyldichlorophosphane by distillation over a substantially unlimited period of time.

EXAMPLE 2

The apparatus and conditions were as in Example 1, except that 2 kg/h of a more highly ethoxylated unbranched $C_{16-18}$ fatty alcohol (molar ratio = 80 $OC_2H_5$ groups per OH group) was added through the conduit 2 to prevent the deposition of solid by-products.

The column 3 was fed with 100 kg/h of a crude product composed of:

18 weight % of methyldichlorophosphane,
2.1 weight % of carbon tetrachloride,
1.0 weight % of chloroform,
0.2 weight % of $POCl_3$, and
0.2 weight % of unidentified constituents, the balance being $PCl_3$. This crude product was worked up so as to recover $CH_3$-$PCl_2$ in continuous operation during which the apparatus could not be found to have been soiled.

EXAMPLE 3

Under the conditions described in Example 1, 2.5 kg/h of an ethylene oxide polymer (molecular weight = 4000) was added through the conduit 2 to prevent the deposition of solid by-products.

100 kg/h of crude product with the composition indicated in Example 1 was worked up so as to recover $CH_3$-$PCl_2$ in continuous operation in the absence of soiling phenomena.

EXAMPLE 4

The apparatus and conditions were as in Example 1, except that 3 kg of a non-ionic surfactant constituted by a copolymer derived from ethylene oxide and propylene oxide (molar ratio = 38:62) was added through the conduit 2 to prevent the deposition of solid by-products.

The column 3 was fed with 100 to 150 kg/h of crude product of the following non-uniform composition (varying within the limits specified):

15 – 20 weight % of methyldichlorophosphane,
1.5 – 3.5 weight % of carbon tetrachloride,
0.5 – 1.5 weight % of chloroform,
0.1 – 0.5 weight % of $POCl_3$, and
0.1 – 0.5 weight % of unidentified constituents, the balance being $PCl_3$. This crude product was worked up so as to recover $CH_3$-$PCl_2$ in continuous operation in the absence of soiling phenomena.

EXAMPLE 5

The apparatus and conditions were as described in Example 1, except that 0.7 kg/h of a barium phenatesulphonate mixture "ADDITIN" RC 1387 (a commercially available product of Rhein-Chemie Rheinau GmbH., Manneheim; "ADDITIN" is a registered Trade Mark of Bayer AG., Leverkusen) was added through the conduit 2 to prevent the deposition of solid by-products. High-boiling material and non-volatile fractions of "ADDITIN" RC 1387 were withdrawn through the conduit 18. 100 kg/h of a crude product with the composition indicated in Example 1 was worked up so as to recover $CH_3$-$PCl_2$ in continuous operation in the absence of soiling phenomena.

EXAMPLE 6

The procedure was as in Example 1, except that neither a non-ionic-surfactant nor a barium phenate-sulphonate mixture (cf. Example 5) was added. After a period as short as a few hours, the efficiency of the circulation evaporators 4 and 12 was found to have been reduced considerably. When the surfactant was withheld for some days, the heating surfaces of the evaporators became heavily encrusted with depositing solid material, so that it was necessary to discontinue distillation and to clean the evaporators.

The above Examples show that reliable continuous production of purified methyldichlorophosphane by distillation is possible if an ionic or non-ionic surfactant is added though not if it is omitted. To ensure reliable operation, it is sufficient to use the surfactant in the proportions indicated in Examples 1 to 5. The use of proportions larger than those indicated therein does not adversely affect reliable operation, but it is good practice to determine the maximum proportion to be employed having due regard to economic considerations.

We claim:

1. A process for recovering methyldichlorophosphane from a mixture containing phosphorus trichloride and methyldichlorophosphane as its principal constituents by distillation in two stages, phosphorus trichloride and other low-boiling material being distilled off overhead in the first stage, methyldichlorophosphane being distilled off from high-boiling material in the second stage, and the latter being fed with base product coming from the first stage, which comprises: dissolving in the said mixture, prior to admitting it to the first distillation stage, 0.01 to 1 weight % of a soluble barium phenate-sulfonate mixture or 0.1 to 10 weight % of a non-ionic surfactant wherein a non-ionic polymer derived from ethylene oxide or from ethylene oxide and propylene oxide or wherein an ethoxylated unbranched fatty alcohol having from 6 to 30 carbon atoms is used as the non-ionic surfactant, and admixing the base product coming from the first distillation stage, prior to admitting it to the second distillation stage, with 1 to 10 weight % of phosphorus oxychloride.

2. A process as claimed in claim 1, wherein 0.5 to 5 weight % of the non-ionic surfactant is dissolved in the said mixture.

3. A process as claimed in claim 1, wherein the said base product is admixed with 3 to 6 weight % of phosphorus oxychloride.

4. A process as claimed in claim 1, wherein base product containing high-boiling material is removed from the second distillation stage, phosphorus oxychloride is distilled off therefrom, and the latter is recycled by being admixed with the base product coming from the first distillation stage.

5. Process as claimed in claim 1, wherein a temperature of at most 115° C is maintained in the base of the first distillation stage.

6. A process as claimed in claim 1, wherein a temperature lower than 120° C is maintained in the base of the second distillation stage.

7. A process as claimed in claim 1, wherein the mixture from which methyldichlorophosphane is recovered is a mixture containing phosphorus trichloride, methyldichlorophosphane, carbon tetrachloride and chloroform.

* * * * *